United States Patent [19]

McDevitt

[11] 4,077,264

[45] Mar. 7, 1978

[54] CONNECTORS FOR MOLTEN METAL SAMPLERS

[76] Inventor: Robert F. McDevitt, P.O. Box 551, Ogden Dunes, Portage, Ind. 46368

[21] Appl. No.: 768,710

[22] Filed: Feb. 15, 1977

Related U.S. Application Data

[62] Division of Ser. No. 720,697, Sep. 7, 1976.

[51] Int. Cl.² ............................................. G01N 1/12
[52] U.S. Cl. ............................................. 73/425.4 R
[58] Field of Search ............... 73/425.4, DIG. 9; 164/4; 249/DIG. 4; 403/210

[56] References Cited

U.S. PATENT DOCUMENTS

| | | | |
|---|---|---|---|
| 3,859,857 | 1/1975 | Falk | 73/425.4 R |
| 3,897,687 | 8/1975 | Boron | 73/425.4 R |

Primary Examiner—S. Clement Swisher

[57] ABSTRACT

The invention involves providing various forms of connectors attachable to a lance for detachably connecting molten metal samplers or devices thereto.

More particularly, the purpose of the invention is to provide a safe and simple method whereby a cast sample for example, through use of an improved connector, may be obtained from a flowing metal stream when molten metal is being transferred by pouring from one type vessel to another. The sample may be used directly for spectographic analysis or can be drilled to provide a sample for wet chemical analysis. In addition, the sample may be sawed and polished for use in metallographic study of grain structure, cleanliness, etc. The entire sample can be cast in a two piece mold assembly or device made of a material with optimum cooling venting and dimensional characteristics.

12 Claims, 14 Drawing Figures

CONNECTORS FOR MOLTEN METAL SAMPLERS

CROSS REFERENCE TO RELATED APPLICATIONS

This application is a division of my copending application Ser. No. 720,697, filed Sept. 7, 1976.

BACKGROUND OF THE INVENTION

In the processing of metals in the molten state it is necessary to obtain a sample representative of the parent material, at various stages in the processing, for the evaluation of either its chemical composition or metallographic structure.

The device or sampler, adopted for attachment to the connector embodying the subject invention, is preferably designed to obtain a quick chilled sample from the flowing metal as it is transferred by pouring from one type vessel to another. It is primarily designed to be used where molten steel is poured from a teeming ladle into a mold.

For many years the typical method of sampling molten metal in the steel industry was to use what was defined as a spoon. The spoon consisted of a deep bowl type ladle or sampler attached to the end of a long handle and made of either cast or forged steel. The spoon varied in size and had a lip to facilitate pouring. In practice the pouring stream was controlled to a slow or partial stream and the spoon was then dipped into the stream of metal to obtain the sample. The spoon was usually tipped into either the right or left side of the stream, whichever was most convenient, and partially filled with molten metal. The molten metal content of the spoon was then poured into a small test mold positioned on the platform. The casting from this mold provided a sample 4 to 8 inches long, tapered, and 1 to 2 inches square in cross-section.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is most pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

SUMMARY OF THE INVENTION

Advantages of the invention or inventions over the spoon technique are:
1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

In view of the foregoing, one of the important objects of the invention is to provide a connector for use with an elongated device for obtaining a sample of a liquid, such as molten metal, which device comprises, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the section. More particularly in this respect, one of the holding means for the sections comprises clip means, and an appendage held in place by this clip means may be utilized for identification purposes and effect release of the clip means, and the means for holding the sections and tubular means may be operated to facilitate disassembly of these components.

Further, each section of the device described above includes a relatively large head portion provided with a recess and an extended portion having a center groove therein so that when the sections are correctly assembled the recesses will form a primary chamber and the grooved extensions will form a tubular formation communicating with the chamber.

An important object of the subject invention is to provide various forms of connectors which are attachable to a lance and serve to detachably support a device in various operative positions.

More particularly, one of the connectors is preferably in the form of an elongated tubular housing having one extremity which is adapted for connection with a lance and an opposite extremity which is provided with a pair of opposed transverse openings for receiving opposite extremities of a device for locating the latter in an operative position substantially transverse to the lance and connector, including means carried by the connector for locking the device in such position.

A specific object is to provide a connector having locking means, as referred to in the preceding paragraph, in which the connector is preferably constructed of a suitable disposable material, such as pasteboard, and the locking means is preferably in the form of integral wing portions of the connector which can be manually flexed or bent to releasably engage the head portion of the device whereby the latter can be locked in either of two positions to locate the entrance of the tubular means in the desired operative position.

Another specific object of the invention is to provide a modified form of connector which is elongated and tubular so that one extremity can be attached to a lance and an opposite extremity which is provided with a side opening and an opposed side slot whereby extremities of a device can be disposed in the opening and slot, with marginal edges of the slot serving to frictionally engage the head of the device for holding the device in an operative position.

Another important object of the invention is to provide a unique setup whereby a connector is so designed and constructed that a lance and/or connector can be manipulated to releasably hold a device in an operation position relative to the connector.

Additional objects and advantages of the invention reside in providing a connector which is safe and efficient to use, and one manufactured on a production basis.

Other objects and advantages will become apparent after the description hereinafter set forth is considered in conjunction with the drawings annexed hereto.

DESCRIPTION OF THE PREFERRED EMBODIMENTS

Figure 1:
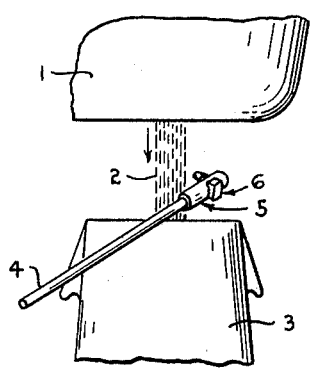
FIG. 1 illustrates a device carried by a lance for use in obtaining a sample of a liquid from a stream thereof.

Referring to FIGS. 1 through 4 and particularly to FIG. 1, there is shown a ladle or vessel 1 containing a hot fluid, such as molten metal, which flows in a stream 2 into a mold 3. A lance 4 is provided with a connector, generally designated 5, and a device generally designated 6, is detachably connected to the connector, and provided with tubular means 7 for disposition in the stream 2 for obtaining a sample therefrom.

The lance 4 is preferably of a length to facilitate manipulation of the device and protect an operator and may be constructed of any material suitable for the purpose but is preferably in the form of an elongated length of pipe.

Figure 4:
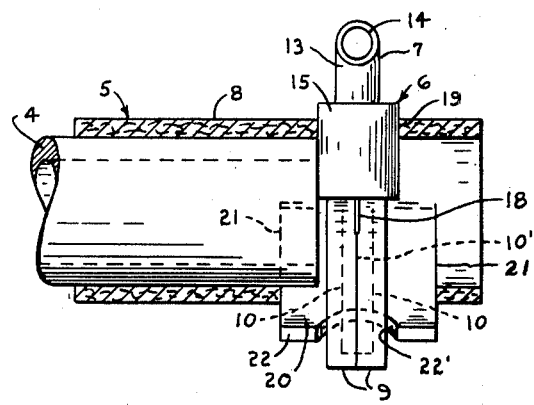
FIG. 4 is a longitudinal section taken substantially on line 4—4 of FIG. 2.
Figure 2:
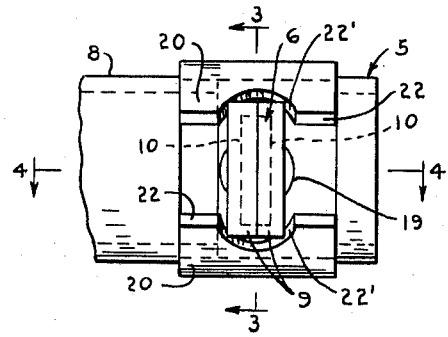
FIG. 2 is a partial side view of a connector on the lance showing one mode of attaching the device to the connector.
Figure 3:
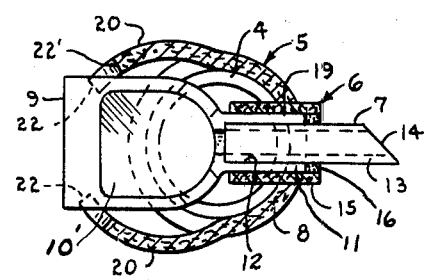
FIG. 3 is a transverse section taken substantially on line 3—3 of FIG. 2.

The connector 5, may be designed and constructed in various ways as will appear hereinafter, but as best shown in FIGS. 2, 3 and 4, it is preferably in the form of a tubular cylindrical member 8 of pasteboard or equivalent material. One extremity of the connector is snugly fitted over an end of the lance and its other extremity serves to detachably support the device 6 in a position transverse to the longitudinal axis of the connector and/or lance.

The device 6 is elongated and is preferably comprised of a pair of moulded half sections, each having an enlarged or head portion 9 provided with a recess 10, and a reduced extended portion 11 provided with a semicylindrical groove 12. When the sections are correctly assembled, the recesses define a chamber 10' and the extended portions 11 and grooves 12 define a tubular formation. The device also preferably includes a tubular means 13, preferably in the form of a cylindrical tube of Pyrex, quartz or equivalent material which has an inner extremity secured in the opening and an outer free extremity provided with a bevelled inlet or entrance 14 for entry into the stream 2. A tubular casing or sleeve 15, preferably of pasteboard, is snugly fitted about the extended portions 11 of the half sections whereby to hold the sections and so that the tubular means 7 is more or less clamped between the extended portions. An apertured member 16 or cement preferably surrounds the tubular means 7 and is snugly fitted or packed into the sleeve and against the portions 11 whereby to prevent entry of molten metal between the sleeve and portions 11 and between the latter and the tubular means. A layer of cement 17, as depicted in FIG. 16 of said continuation, may also be utilized to secure a tubular means in a tubular formation or a casing about the tubular formation. It should be noted that the sections are provided with mating notches whereby to provide vents 18 (one shown) at the sides of the heads 9. It may also be noted that the head portions having planar parallel side surfaces, planar end surfaces and rounded surfaces which merge into the extended portions 11. The extended portions may be referred to as channel portions which form a tubular formation which receives the tubular means 7.

Referring back to the tubular member 8 which constitutes the connector 5, it is provided with a round side opening 19 for accommodating the sleeve or casing 15 of the device as depicted in FIG. 3 and 4 and with a pair of curved wings or outwardly extending portions 20 disposed generally opposite or across from the opening 19. These wings or portions 20 are formed by providing the member with an opening opposite to the opening 19 and by cutting the member 8 along parallel lines 21 transverse to the longitudinal axis of the member and by a longitudinal parting line which extends through the opening opposite the opening 19 so that the portions 20 can be bent outwardly whereby the parting line will form marginal edges 22 on the wings and the opening opposite the opening 19 will define a pair of arcuate notches 22' interrupting the edge 22. The wing portions may be considered to be resiliently flexible or yieldable in character so that they can be manually spread apart in order that the parallel side edges of the head portions 9 will be received and gripped in the notch as evidenced in FIGS. 2, 3 and 4 to hold the device in a position substantially transverse to the longitudinal axis of the connector and/or lance so that an operator standing safely at one side or offside of the stream 2 can readily manipulate the lance to cause the entrance 14 of the device to enter the stream whereby to obtain a sample thereof as distinguished from at least some other equipment in use which requires an operator to stand in what may be termed a dangerous position to obtain a sample. The lance or member 8 may be moved with respect to one another to cause an inner end of the lance to engage the sleeve 15 of the device as best shown in FIG. 4 whereby to assist in stabilizing or holding the device in relation to the member. It should be noted that the wing portions 20 are preferably spread apart sufficiently so that the sleeve 15 of the device can be inserted into the opening 19 and the head portions 9 into the notches 22' by a single thrust of the device, or if desired the wings may be opened to a lesser extent to permit entry of the sleeve into the opening 19 so that the planar faces of the head portions will engage the opposed marginal edges 22 of the wings whereupon the device may be rotated 90° to cause the wings to spread apart in order that their notches 22' will receive the edges of the head portions. It should also be noted that the device is preferably inset from the outer end of the tubular connector a sufficient distance so that any normal charring or disintegration of the outer end resulting from engagement with any molten metal will not accidently release the device. Of further significance is the fact that the wing portions also assist in holding the half sections assembled and promote safety as they also serve as shields to protect the half sections from spraying metal as well as an operator using the device.

Figure 5:
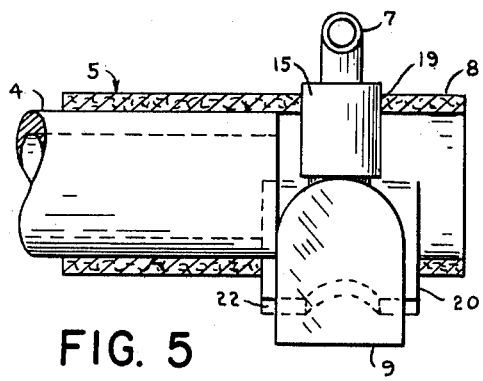
FIG. 5 is a longitudinal sectional view of a connector and a portion of a lance depicting an alternative mode of attaching the device to the connector.

If so desired, the device can be assembled with the connector as exemplified in FIG. 5, whereby the marginal end portions 22 of the wings (one shown) will engage or grip the planar side surfaces of the head portions of the sections and an end of the lance may engage the head portions.

After a sample is obtained, the device may be readily released from the connector by merely bending back or breaking the wings and pulling the sleeve out of the opening 19 and so that the sleeve 15 and tubular means may be separated from one another including the half sections, the tubular means may be separated from a stem portion of a sample and the head portions of the sections may be released from a head portion of a sample which is joined to the stem portion.

Figure 6:
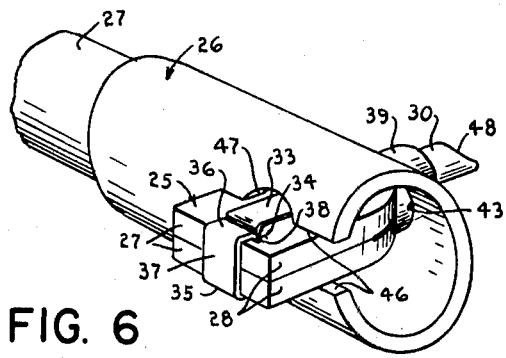
FIG. 6 is a perspective view of a modified form of connector and a sampling device which is attachable to the connector in a mode different from those shown in FIGS. 4 and 5.
Figure 7:
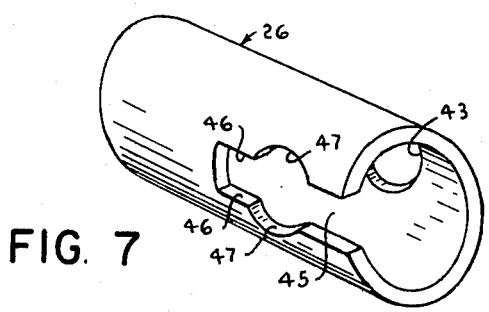
FIG. 7 is a perspective view of the connector illustrated in FIG. 6.
Figure 8:
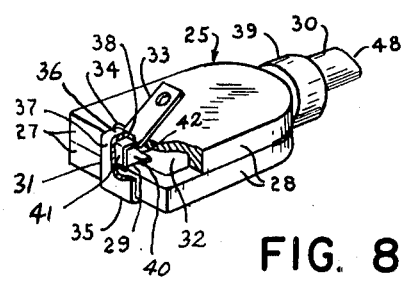
FIG. 8 is a perspective view of the device shown in FIG. 6.

Referring to FIGS. 6, 7 and 8 there is disclosed a modified device generally designated 25 and a modified form of a connector generally designated 26. The connector 26 is adapted for a telescoping relatively tight fit on an end of a lance 27.

The device 25 is substantially the same as the device 6 above referred but differs therefrom in that end portions 27 of its half sections 28 are provided with notches 29 (one shown) which forms a generally rectangular opening axially aligned with the longitudinal axis of a tubular receiving means 30 and through which extends a sheet metal appendage 31, preferably rectangular in cross-section, so that an inner portion of the appendage is located in a chamber 32 formed by the head portions 28 of the sections and an outer portion 33 provided with an aperture is located exteriorly of the head portions to which a tab may be attached for identification purposes. The notches 29 are similar to those identified as 234 in FIG. 17 and 18 of said continuation. The outer planar side surfaces of the head portions 28 adjacent to the notches 29 are preferably respectively provided with transversely disposed corresponding grooves 34 (one shown) so that resiliently flexible clip means 35 having legs 36 joined by a bridge 37 embrace portions of the head portions and so that detents 38 formed on the ends of the legs may be manually located or snapped in the grooves 34. This clip means serves to hold the head portions together at one extremity of the device and a sleeve or casing 39 serves to hold the channel or extended portions at the other extremity of the device together and about the tubular means 30. The clip means also serves to cause a portion 40 of the appendage 31 to be locked in the notches 29, a portion 41 to be locked between the sections and the clip means, and an indented portion 42 of the appendage in one of the grooves 34. This appendage and clip means are substantially the same as those shown in FIG. 15 in said continuation. The free outer portion 31 not only serves as a means whereby identification means may be attached thereto but is a handle which can be manually grasped or pulled by a tool whereby to release the clip means from the half sections. Obviously, the appendage per se may serve as an identification means.

The connector 26 is similar to the connector 5, described above, and is provided with a round side opening 43 which receives the sleeve 29 of the device and with an elongated notch 45 having parallel longitudinal marginal edges 46, which edges are respectively interrupted by arcuate notches 47 which define a generally round opening opposite the opening 43 whereby the head portions 28 of the device may be manually inserted into the elongated notch whereby the planar side surfaces of the head portions may be caused to engage the edges 46 to hold the device in a position substantially transverse to the longitudinal axis. The opening formed by the arcuate notches 47 obviously afford clearance to facilitate entry of the sleeve 29 through the opening 43. The tubular means 30 is provided with a bevelled entrance 48.

Attention is directed to the fact that the plane of the bevelled entrance 48 of the device 25 is so disposed with reference to the chamber 32 formed by the head portions of the half sections that the inflow of metal or liquid into the chamber is generally more in a horizontal plane, as distinguished from a generally vertical plane when the head portions are disposed as shown in FIG. 4.

Figure 9:
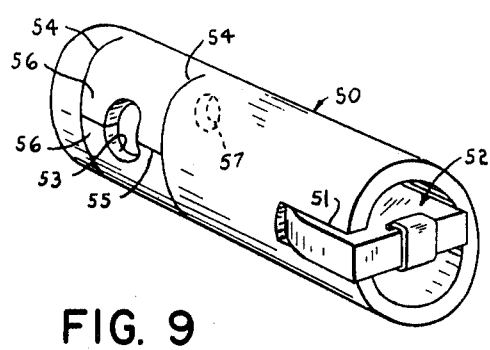
FIG. 9, depicts a perspective view of modified form of connector illustrating how the device shown in FIG. 2 can be stored therein for shipment.
Figure 10:
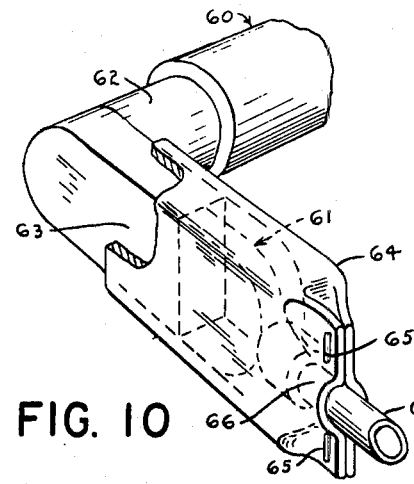
FIG. 10 is a perspective view of a modified form of a connector for a device.
Figure 11:
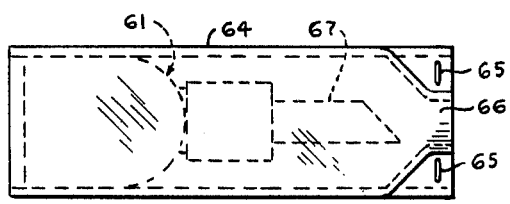
FIG. 11 is a side view of the device shown in FIG. 10.

A modified form of a connector generally designated 50 is depicted in FIG. 9. This connector comprises a relatively long cylindrical member having one extremity which is provided with a longitudinal slot 51 of a predetermined width and length in order to accommodate side edge portions of the head portions of half sections of a device generally designated 52, when the latter is substantially confined in the member. This setup affords protection for the device during shipment or storage prior to use.

The opposite extremity of the connector is provided with an opening 53 aligned with the slot 51, a pair of transverse parallel cuts or scores 54 on opposite sides of the opening and a longitudinal cut or score 55 intersecting the opening so that portions 56 of the member may be bent outwardly to provide wing portions provided with notches in a manner substantially in accord with the structure shown in FIG. 2 for accommodating the head portions of the device in either of the two positions depicted in this FIG. and FIG. 5. The member is also provided with a side opening 57 opposite the opening 53 for accommodating a fore extremity of the device as shown in FIG. 9. The foregoing structure is unique in that the device is protected substantially within the confines of the connector until it is removed and installed in the connector for use. Obviously, the lance is inserted into the slotted extremity of the connector after the device is removed from its storage position and installed to its operative position.

Figure 12:
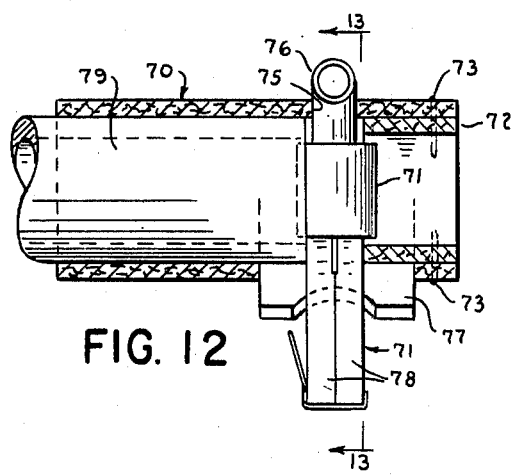
FIG. 12 is a longitudinal section of a modified form of a lance and connector and the device of FIG. 8 which is more or less jointly held against accidental displacement by the lance and connector.
Figure 13:
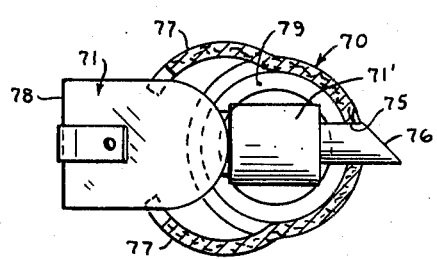
FIG. 13 is a transverse section taken substantially on line 13—13 of FIG. 12.

FIGS. 12 and 13 disclose a modified form of connector generally designated 70 for accommodating a device generally designated 71 which substantially corresponds to the device shown in FIG. 8 above referred to.

The connector 70 preferably comprises a cylindrical tubular member provided with an internal abutment means, preferably in the form of an annular ring or element 72 of pasteboard or equivalent material, which is secured in place in the member by staples 73 or equivalent means, or cement. The connector or member 70 is also provided with an opening 75 for accommodating a tubular means 76 of the device and with wings 77 opposite the opening for accommodating head portions 76 of the device. The connector is unique in that the opening 75 receives the tubular means 76 in lieu of the sleeve 71' as depicted in FIG. 3. The setup also affords a support for the tubular means in use and assists in preventing any seepage of metal or fluid into the chamber of the device between the tubular means and half sections. Another feature resides in the abutment means 72 which receives a portion of the sleeve 71' and engages one of the half sections and a portion of the sleeve is also disposed in an open end of a tubular lance 79 as depicted in FIG. 12 whereby to lock the device in a correct operative position for use. Obviously, the lance may be shifted to the position shown in FIG. 12, after the device is placed in the connector. If the abutment means is secured in position prior to entry of the device then it may become necessary to slightly cock the device so that the sleeve 71' may be correctly located in the abutment means when the wings 77 are spread apart. The device may be assembled with the connector as shown in FIGS. 12 and 13 or in a different position, such as the one shown in FIG. 5.

Figure 14:
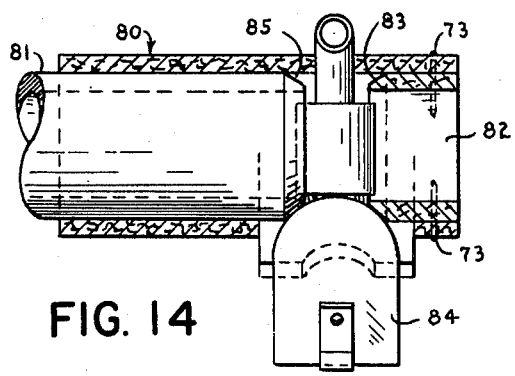
FIG. 14 is a longitudinal sectional view of a modified form of lance and connector showing another example or mode of attaching the device of FIG. 8 thereto.

FIG. 14 depicts a modified form of a connector generally designated 80 and a lance 81 which substantially respectively correspond to those shown in FIGS. 12 and 13, except that an abutment means 82 is preferably bevelled at its inner end as indicated at 83 whereby to facilitate its entry into the connector and engage curved portions of head portions of a device 84 and the inner end of the lance is preferably bevelled at 85 for also engaging the curved portions and facilitating entry of the lance into the connector, all for the purpose of holding the device in the position shown, which position is different from the one shown in FIG. 12. The lance may be shifted to the position shown to lock the device in place after the latter has been inserted into the connector.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. An elongated nonmetallic connector having one extremity for attachment to a lance and an opposite extremity provided with a first opening for receiving one end of an elongated device for sampling a liquid and with a second opening located opposite the first opening for receiving an opposite end of said device for locating the latter in an operative position for use substantially transverse to the longitudinal axis of said connector.

2. The connector defined in claim 1, including means provided on said connector operatively related to said second opening whereby to assist in holding such a device in said position and protecting it when inserted into the liquid.

3. The connector defined in claim 1, including means integral with said connector for manual movement to a position to permit entry of said opposite end of the device into said second opening and to another position for holding the device in said operative position.

4. The connector defined in claim 1, in which said connector is tubular and provided with at least one integral portion adjacent said second opening which can be manually moved whereby to releasably hold the device in said operative position.

5. The connector defined in claim 1, in which said connector is tubular and elongated sufficiently to contain such a device prior to manipulating the latter to its operative position, said connector is provided with a pair of integral wing portions adjacent said second opening which can be moved whereby to releasably hold the device in said operative position, and said wing portions are at least partially the result of providing said second opening.

6. An elongated nonmetallic connector having a tubular extremity provided with a first side opening for receiving one end of an elongated device for sampling a liquid and with a second side opening opposite said first opening for receiving an opposite end of the device for locating the latter in an operative position for use substantially transverse to the longitudinal axis of said connector.

7. An elongated nonmetallic connector having a tubular extremity provided with oppositely disposed side openings for respectively accommodating opposite ends of an elongated device for sampling a liquid and so that the device is located in an operative position for use substantially transverse to the longitudinal axis of said connector.

8. The connector defined in claim 7, in which one of said openings has opposed marginal edges for frictionally engaging the device whereby to assist in holding the device in the operative position.

9. The connector defined in claim 7, in which said connector is provided with internal means for accommodating a portion of a device whereby to assist in preventing movement of the device in a direction transverse to said axis.

10. The connector defined in claim 7, in which said connector has an opposite tubular extremity for accommodating an end of a lance for engagement with such a device whereby to assist in holding the device in said operative position.

11. An elongated connector having a tubular extremity provided with a first relatively small side opening through which a tubular means of Pyrex, quartz or equivalent material of an elongated device for sampling a liquid extends for initially receiving the liquid, said extremity also being provided with a second side opening which is larger and opposite said first opening for accommodating a relatively larger portion of the device whereby the latter can be held in an operative position for use substantially transverse to the longitudinal axis of said connector.

12. The connector defined in claim 11, in which the side openings are of such a character that the device can be adjusted in said openings to either one of two operative positions.

* * * * *